United States Patent [19]

Liu et al.

[11] Patent Number: 5,225,485
[45] Date of Patent: Jul. 6, 1993

[54] POLYETHERIMIDE ESTER SUTURE AND ITS METHOD OF MANUFACTURE AND METHOD OF USE

[75] Inventors: Cheng-Kung Liu, Norwalk; John C. Brewer, Bristol, both of Conn.

[73] Assignee: United States Surgical Corporation, Norwalk, Conn.

[21] Appl. No.: 845,100

[22] Filed: Mar. 3, 1992

[51] Int. Cl.⁵ .............................................. C08K 5/00
[52] U.S. Cl. .................................... 523/111; 528/289; 606/230
[58] Field of Search ................ 606/230; 528/289; 523/111

[56] References Cited

U.S. PATENT DOCUMENTS

| | | | |
|---|---|---|---|
| Re. 32,770 | 10/1988 | Kaplan | 128/335.5 |
| 3,621,076 | 11/1971 | De Winter et al. | 260/857 |
| 3,630,205 | 12/1971 | Listner | 128/335.5 |
| 4,209,607 | 6/1980 | Shalaby et al. | 528/291 |
| 4,221,703 | 9/1980 | Hoeschele | 260/45.9 |
| 4,224,946 | 9/1980 | Kaplan | 128/335.5 |
| 4,226,234 | 10/1980 | Shalaby | 606/230 |
| 4,246,904 | 1/1981 | Kaplan | 128/335.5 |
| 4,252,920 | 2/1981 | Deleens et al. | 525/430 |
| 4,314,561 | 2/1982 | Kaplan | 128/335.5 |
| 4,332,920 | 6/1982 | Foy et al. | 525/408 |
| 4,343,931 | 8/1982 | Barrows | 528/291 |
| 4,371,692 | 2/1983 | Wolfe, Jr. | 528/289 |
| 4,371,693 | 2/1983 | Wolfe, Jr. | 528/292 |
| 4,511,706 | 4/1985 | Shalaby et al. | 528/192 |
| 4,556,705 | 12/1985 | McCready | 528/289 |
| 4,578,451 | 3/1986 | Weaver et al. | 528/292 |
| 4,608,428 | 8/1986 | Shalaby et al. | 528/192 |
| 4,769,273 | 9/1988 | Hoeschele et al. | 428/215 |
| 4,867,679 | 9/1989 | Rackley | 433/15 |
| 4,868,062 | 9/1989 | Hoeschele | 428/423.1 |
| 4,892,774 | 1/1990 | Vallance | 428/174 |
| 4,911,165 | 3/1990 | Lennard et al. | 606/231 |
| 5,102,419 | 4/1992 | Gertzman et al. | 606/228 |
| 5,147,382 | 9/1992 | Gertzman et al. | 606/228 |

Primary Examiner—Thurman K. Page
Assistant Examiner—William E. Benston
Attorney, Agent, or Firm—Thomas R. Bremer

[57] ABSTRACT

A polyetherimide suture exhibits excellent properties such as resistance to creep, great knot security and physical stability. The suture may be monofilament or multifilament, and methods of making and using the suture are disclosed.

15 Claims, 1 Drawing Sheet

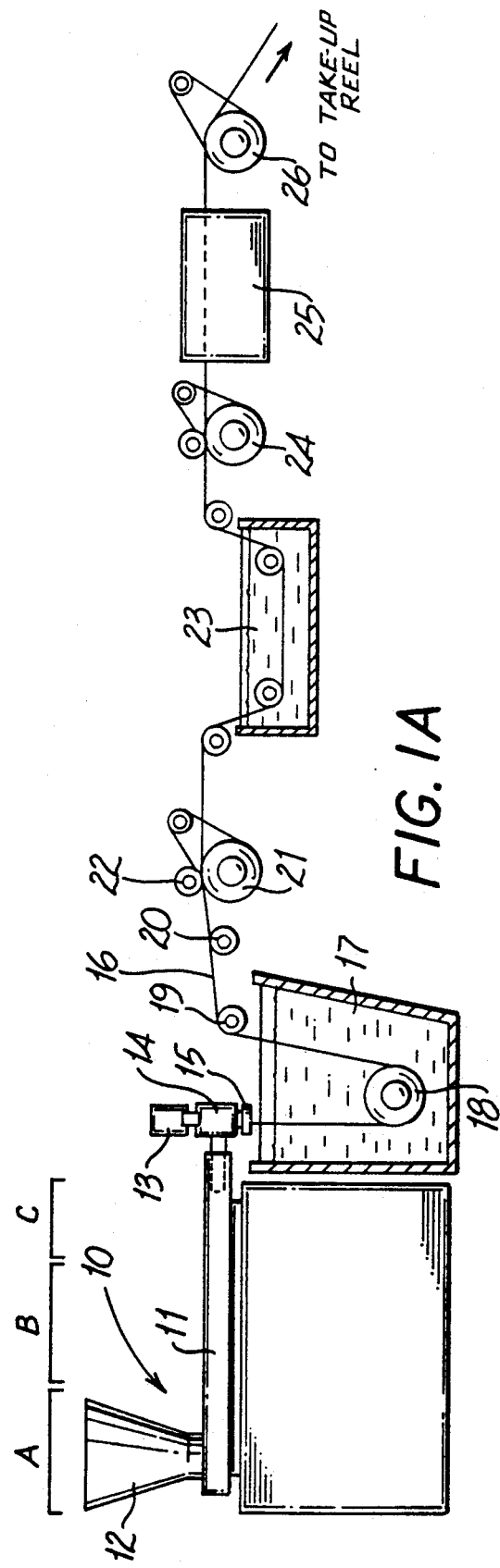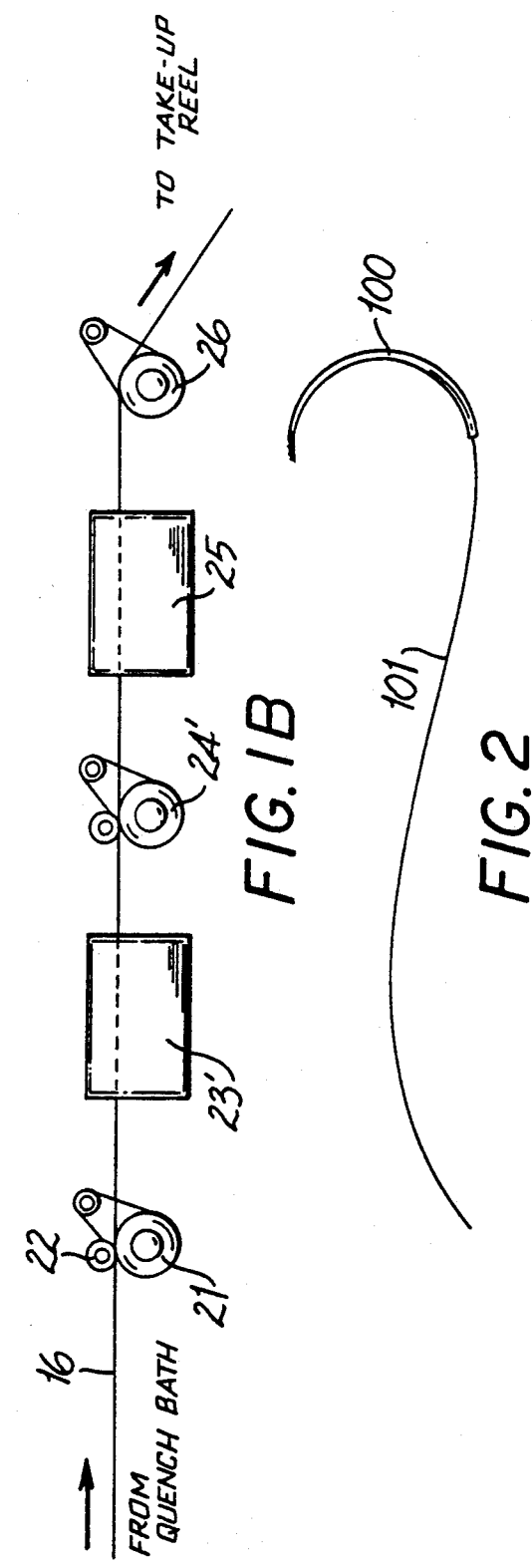

POLYETHERIMIDE ESTER SUTURE AND ITS METHOD OF MANUFACTURE AND METHOD OF USE

TECHNICAL FIELD

The present invention relates to non-bioabsorbable surgical sutures and more particularly to both monofilament and multifilament polyetherimide ester sutures.

BACKGROUND OF THE INVENTION

Non-bioabsorbable fibers are known in the art. However, in the manufacture of sutures one important characteristic of a suture is the amount of effort typically required to straighten the suture upon its removal from the package in order to ready the suture for use. This effort appears to be related to the "strain energy" of the suture, i.e., the integration of the stress-strain curve for the suture measured in kilogram-mm, and is equivalent to the work expended in elongating the monofilament by a specified percentage of its original length. As the strain energy of a given size of suture decreases so, too, does the amount of effort required to straighten the suture prior to use. A decrease in strain energy also appears to relate to the perceived flexibility of the suture, another important characteristic.

Another important characteristic of a suture is its ability to retain a knot. In general, a suture exhibiting greater knot security is preferred to one exhibiting a lesser degree of knot security. Similarly, a suture must exhibit favorable straight tensile strength, loop strength and knot strength.

A further important consideration in the manufacture and use of sutures is that the physical properties of the suture should not change significantly during use. By way of example, under the tension of a surgeon's knot used for wound closure, a suture may undergo stretching which will cause the suture to stretch or elongate, a phenomenon referred to herein as "creep".

Therefore, it would be advantageous to provide a non-bioabsorbable suture which exhibits favorable physical properties as well as a high degree of physical stability, including resistance to creep.

SUMMARY OF THE INVENTION

In accordance with the present invention, there are provided both monofilament and multifilament sutures manufactured from a polyetherimide ester composition comprising at least about 30 mole percent, preferably at least about 50 mole percent, and most preferably at least about 70 mole percent the reaction product of a) at least one low molecular weight diol, b) at least one dicarboxylic acid and, c) at least one polyoxyalkylene diimide diacid.

In another aspect of the present invention there is provided a process for manufacturing a polyetherimide ester suture exhibiting excellent energy and/or increased knot security for a given size comprising the operations of extruding polyetherimide ester resin at an extrusion temperature of from about 190° C. to about 240° C. to provide a monofilament fiber, stretching the solidified monofilament at a temperature of from about 30° C. to about 98° C. in water (or other suitable liquid medium) or at from about 30° C. to about 180° C in air (or other suitable gaseous medium) at a stretch ratio of from about 3;1 to about 7:1 to provide a stretched monofilament. The stretched monofilament optionally may be annealed with or without relaxation at a temperature of from about 60° C. to about 180° C. to provide the finished suture.

BRIEF DESCRIPTION OF THE DRAWINGS

FIG. 1A is a schematic illustration of apparatus which is suitable for manufacturing the polyetherimide ester monofilament suture of this invention; and, FIG. 1B is a modification of the apparatus of FIG. 1A which is particularly suitable for the manufacture of polyetherimide ester monofilaments of smaller size, e.g., sizes 4/0 and smaller.

FIG. 2 is a perspective view of a suture of the present invention attached to a needle.

DESCRIPTION OF THE PREFERRED EMBODIMENTS

Suitable polyetherimide ester compositions from which the suture of the present invention can be manufactured include either random or block polymers prepared by conventional processes from a) at least one diol, b) at least one dicarboxylic acid, and c) at least one polyoxyalkylene diimide diacid. Preferred compositions from which the suture of the present invention can be manufactured may be prepared from a) at least one $C_2$-$C_{15}$ aliphatic and/or cycloaliphatic diol, b) at least one $C_2$-$C_{16}$ aliphatic, cycloaliphatic and/or aromatic dicarboxylic acid or ester derivatives thereof and c) at least one polyoxyalkylene diimide diacid. The amount of polyoxyalkylene diimide diacid employed is generally dependent upon the desired properties of the resultant polyetherimide ester. In general, the weight ratio of polyoxyalkylene diimide diacid to dicarboxylic acid is from about 0.25 to 2, and preferably from about 0.4 to about 1.4. The compositions optionally may contain and preferably do contain additional stabilizers for even greater stabilization.

Suitable diols for use in preparing the compositions suitable for use in the manufacture of the present invention include saturated and unsaturated aliphatic and cycloaliphatic dihydroxy compounds as well as aromatic dihydroxy compounds. These diols are preferably of a low molecular weight, i.e. having a molecular weight of about 250 or less. When used herein, the term "diols" and "low molecular weight diols" should be construed to include equivalent ester forming derivatives thereof, provided, however, that the molecular weight requirement pertains to the diol only and not to its derivatives. Exemplary of ester forming derivatives are the acetates of the diols as well as for example ethylene oxide or ethylene carbonate for ethylene glycol. The most preferred diol is 1, 4 butane diol.

Dicarboxylic acids which are suitable for use in the practice of the present invention include aliphatic, cycloaliphatic, and aromatic dicarboxylic acids. These acids are preferably of a low molecular weight, i.e., having a molecular weight of less than about 300; however, higher molecular weight dicarboxylic acids, especially dimer acids, may also be used. The term "dicarboxylic acids" as used herein, includes equivalents of dicarboxylic acids having two functional carboxyl groups which perform substantially like dicarboxylic acids in reaction with glycols and diols in forming polyester polymers. These equivalents include esters and ester-forming derivatives, such as acid halides and anhydrides. The molecular weight preference, mentioned above, pertains to the acid and not to its equivalent ester or ester forming derivative. Thus, an ester of a dicarboxylic acid having a molecular weight greater than 300 or an acid equivalent of a dicarboxylic acid having a molecular weight greater than 300 are included provided the acid has a molecular weight below about 300. Additionally, the dicarboxylic acids may contain any substituent group(s) or combinations which do not substantially interfere with the polymer formation and use of the polymer in this invention. Especially preferred as a dicarboxylic acid is dimethyl terephthalate.

Polyoxyalkylene diimide diacids suitable for use herein are high molecular weight diimide diacids wherein the average molecular weight is greater than about 700 and preferably greater than about 900. They may be prepared by the imidization reaction of one or more tricarboxylic acid compounds containing two vicinal carboxyl groups or an anhydride group and an additional carboxyl group which must be esterifiable and preferably is nonimidizable with a high molecular weight polyoxyalkylene diamine. The polyoxyalkylene diimide diacids useful herein are of the following formula

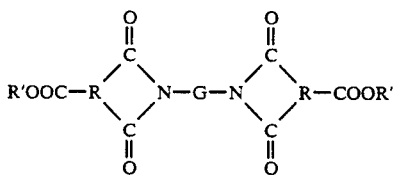

wherein each R is independently a trivalent organic radical. Preferably R is a $C_2$ to $C_{20}$ aliphatic, aromatic or cycloaliphatic trivalent organic radical; each R' is independently hydrogen or a monovalent organic radical preferably selected from the group consisting of $C_1$ to $C_6$ aliphatic, cycloaliphatic radicals and $C_6$ to $C_{12}$ aromatic radicals, e.g. benzyl, most preferably hydrogen; and G is the radical remaining after the removal of the terminal (or as nearly terminal as possible) hydroxy groups of a long chain ether glycol having an average molecular weight of from about 600 to about 12000, preferably from about 900 to about 4000, and a carbon-to-oxygen ratio of from about 1.8 to about 4.3. Such long chain ether glycols include for example polypropylene ether glycol and co(polyethylene ether-propylene ether) glycol having a predominantly polyethylene ether backbone. Especially preferred for the tricarboxylic acid component is trimellitic anhydride. Compositions useful in making the sutures of the present invention are available from General Electric Company under the trade name LOMOD. Particularly preferred is LOMOD TE 3070A. These and other suitable compositions are disclosed and claimed in U.S. Pat. No. 4,556,705.

Multifilament sutures of the present invention may be made by methods known in the art. Braid constructions such as those disclosed and claimed in U.S. Pat. Nos. 5,059,213 and 5,019,093 are suitable for the polyetherimide ester multifilament suture of the present invention.

A suitable process for the manufacture of polyether imide ester monofilament sutures of the present invention comprises the operations of melt extruding the polyetherimide ester resin at an extrusion temperature of from about 190° C. to about 240° C. to provide a monofilament, stretching the solidified monofilament at a temperature of from about 30° C. to about 98° C. in water (or other suitable liquid medium) or at from about 30° C. to about 180° C. in air (or other suitable gaseous medium) at a stretch ratio of from about 3:1 to about 7:1 to provide a stretched monofilament. Optionally, the monofilament may then be annealed at a temperature of from about 60° C. to about 180° C. to provide the finished suture, the annealing resulting in shrinkage of the stretched monofilament for a recovery to within about 75 to about 97 percent of the length of the monofilament prior to annealing.

FIG. 1A schematically illustrates a polyetherimide ester monofilament suture manufacturing operation which is especially suitable for producing larger size sutures, e.g., those of sizes 3/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polyetherimide ester resin are introduced to the extruder through hopper 12. Any of the polyetherimide esters which are useful for the formation of fibers can be used herein.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to reduce the length of the air gap, e.g., to from 1 to 10 cm, thereby isolating monofilament 16 from contact with air currents which might otherwise affect the cooling of the monofilament in an unpredictable manner. In general, barrel zone A of the extruder can be maintained at a temperature of from about 190° C. to 220° C., zone B at from about 200° C. to 230° C. and zone C at from about 210° C. to about 240° C. Additional temperature parameters include: metering pump block 13 at from about 200° C. to about 240° C., spin pack 14 at from about 205° C. to about 240° C., spinneret 15 at from about 210° C. to about 240° C. and quench bath at from about 25° C. to about 90° C.

Monofilament 16 is passed through quench bath 17 around driven roller 18 and over idel rollers 19 and 20. Optionally, a wiper (not shown) may remove excess water from the monofilament as it is removed from quench bath 17. On exiting the quench bath the monofilament is wrapped around a first godet 21 provided with nip roll 22 to prevent slippage which might otherwise result from the subsequent stretching operation. Monofilament 16 passing from godet 21 is stretched, e.g., with stretch ratios on the order of from about 3:1 to about 7:1 and preferably from about 4:1 to about 6:1, to effect its orientation and thereby increase its tensile strength. In the stretching operation shown in FIG. 1A, generally suitable for larger size sutures, e.g., sizes 2 to 3/0, monofilament 16 is drawn through hot water draw bath 23 by means of second godet 24 which rotates at a higher speed than first godet 21 to provide the desired stretch ratio. The temperature of hot water draw bath 23 is advantageously from about 30° C. to about 98° C. and preferably is from about 60° C. to about 98° C.

In the alternative stretching operation shown in FIG. 1B, generally preferred for smaller sutures sizes, e.g., sizes 4/0 to 8/0, monofilament 16 is drawn by second godet 24' through hot air convection oven chamber 23' at a temperature of from about 30° C. to about 180° C. and preferably from about 100° C. to about 140° C. to provide the desired amount of stretch. Following the stretching operation shown in FIG. 1A or 1B, monofilament 16 optionally may be subjected to an on-line annealing without shrinkage or relaxation with shrinkage operation as a result of which the monofilament shrinks. In the processes of FIGS. 1A and 1B, on line annealing with or without relaxation when desired is accomplished by driving monofilament 16 by third godet 26 through second hot air oven chamber 25 at a temperature of from about 60° C. to about 180° C. and preferably from about 120° C. to about 180° C. At these temperatures, monofilament 16 will generally recover to within about 75 to about 97 percent, and preferably to within about 95 percent, of its pre-annealed length to provide the finished suture. For relaxation, the third godet rotates at a slower speed than the second godet thus relieving tension on the filament.

The suture of the present invention, suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is further within the scope of this invention to incorporate one or more medico-surgically useful substances into the present invention, e.g., those which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulphate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the sutures of the present invention in order to increase visibility of the suture in the surgical field. Dyes known to be suitable for incorporation in sutures can be used. Such dyes include but are not limited to Logwood extract and D & C Green No. 6 as described in the handbook of *U.S. Colorants for Food, Drugs and Cosmetics*, by Daniel M. Marrion (1979). Preferably, sutures in accordance with the invention are dyed by adding up to about a few percent and preferably about 0.75% dye, such as D&C Green No. 6 to the resin prior to extrusion.

In order that those skilled in the art may be better able to practice the present invention, the following examples are given as an illustration of the preparation and superior characteristics of the polyetherimide ester sutures of the present invention. It should be noted that the invention is not limited to the specific details embodied in the examples and further that all ratios or parts recited are by weight.

EXAMPLE 1

Table I below sets forth typical conditions for extruding, stretching various sizes of polyethermide sutures in accordance with this invention. All of the monofilament sutures were fabricated from LOMOD resin TE3070A-1001 (a polyetherimide ester commercially available from General Electric Co.)

TABLE I

CONDITIONS OF MANUFACTURING VARIOUS SIZES OF POLYETHERIMIDE ESTER MONOFILAMENT

| Example | 1 |
|---|---|
| Suture Size | 3/0 |
| Process Conditions | Extrusion Operation |
| extruder screw, rpm | 6.0 |
| pump rpm | 12.1 |
| driven roller, rpm | 7.0 |
| barrel temp., °C., zone A | 210 |
| barrel temp., °C., zone B | 215 |
| barrel temp., °C., zone C | 220 |
| clamp temp., °C. | 220 |
| adapter temp., °C. | 220 |
| pump temp., °C. | 220 |
| block temp., °C. | 220 |
| barrel melt temp., °C. | 223 |
| pump melt temp., °C. | 221 |
| spinneret melt temp., °C. | 237 |
| barrel pressure, psi | 3030 |
| Process Conditions | Extrusion Operation |
| pump pressure, psi | 2960 |
| spinneret pressure, psi | 1050 |
| pump size, cc per revolution | 0.584 |
| diameter of spinneret orifices, mm | 0.75 |
| no. of spinneret orifices | 4 |
| quench bath temp., °C. | 46 |
| depth of driven roller | 23 |
| filter (candle) | 12 |
| | Stretching (Orienting) Operation |
| draw bath temp., °C. | 98 |
| first godet, mpm | 10.1 |
| second godet, mpm | 55.5 |
| draw ratio | 5.5 |

The physical properties of the sutures and the procedures employed for their measurement are set forth in Table II as follows:

TABLE II

PROCEDURES FOR MEASURING PHYSICAL PROPERTIES OF POLYETHERIMIDE ESTER MONOFILAMENT SUTURES

| Physical Property | Test Procedure |
|---|---|
| knot pull, tensile strength, kg | U.S.P. XXI, tensile strength, sutures (881) |
| straight pull, kg | ASTM D-2256, Instron Corportion |
| elongation at break, % | ASTM D-2256 |
| tensile strength, kg/mm$^2$ | ASTM D-2256, Instron Corportion Series IX Automated Materials Testing System 1.03A |
| 0–5% and 0–10% strain energies, kg-mm | ASTM D-2256, Instron Corporation Series IX Automated Materials Testing System 1.03A |
| knot security | A 2 cm loop is tied with a surgeon's square knot (1 = 1 = 1 = 1) securing the throws at 20% of the USP XXII knot strength for 2/0 nonabsorbable sutures (n = 10 loops |

TABLE II-continued

PROCEDURES FOR MEASURING PHYSICAL PROPERTIES OF POLYETHERIMIDE ESTER MONOFILAMENT SUTURES

| Physical Property | Test Procedure |
| --- | --- |
|  | per group). The loop is placed next to a cloth-wrapped mandrel rotating at .5 rpm. The fixtures are secured to allow contact of the cloth material against the fourth, i.e. top throw of each knot. The cloth wrapping is moistened with 37° C. water prior to the test and is periodically remoistened during the test. Each pass of the cloth across the knot (for a total of 100 passes), the knot is inspected for top throw security. For a knot to be considered secure, the 3 mm ears must not come undone and there must be no relaxation of the knot or loss of the fourth throw. |
| Melt Flow | ASTM D-1238 |

Table III below sets forth the physical properties of the size 3/0 polyetherimide ester suture of the present invention.

TABLE III

| Physical Property | Ex. 1 |
| --- | --- |
| diameter (mm) | 0.241 |
| knot-pull (kg) | 1.11 |
| Straight-pull (kg) | 1.64 |
| Strain Energy 0–5% (kg-mm) | 0.92 |
| Strain Energy 0–10% (kg-mm) | 3.00 |
| Elongation (%) | 29.0 |
| Tensile Strength (kg/mm$^2$) | 35.9 |
| Knot Security* | 0/10 |

*Number of knot failures out of 10 samples.

The yarn of Example 1 was placed under 1.8 g/den constant tension in a water bath at temperature of 37° C. At the time intervals listed below, the percent elongation, or "creep", was measured. Table IV illustrates the physical stability of the polyetherimide ester.

TABLE IV

| | Creep, % |
| --- | --- |
| 5 min | 0.0 |
| 10 min | 0.3 |
| 30 min | 0.3 |
| 45 min | 0.3 |
| 60 min | 0.3 |

Obviously, other modifications and variations of the present invention are possible in light of the above teachings. It is therefore to be understood that changes may be made in particular embodiments of the invention described which are within the full intended scope of the invention as defined by the claims.

What is claimed is:

1. A suture manufactured from a polyetherimide ester composition which comprises at least about 30 mole percent the reaction product of
   a) at least one low molecular weight diol;
   b) at least one dicarboxylic acid; and
   c) at least one polyoxyalkylene diimide diacid.

2. A suture according to claim 1 wherein the diol is selected from a member of the group consisting of a $C_2$ to $C_{15}$ aliphatic diol, a $C_2$ to $C_{15}$ cycloaliphatic diol and mixtures thereof.

3. A suture according to claim 2 wherein the diol is 1,4 butane diol.

4. A suture according to claim 1 wherein the dicarboxylic acid is selected from a member of the group consisting of $C_2$ to $C_{16}$ aliphatic dicarboxylic acids, $C_2$ to $C_{16}$ cycloaliphatic dicarboxylic acids, $C_6$ to $C_{16}$ aromatic dicarboxylic acid, ester derivatives thereof and mixtures thereof.

5. A suture according to claim 1 wherein the dicarboxylic acid is dimethyl terephthalate.

6. A suture according to claim 1 wherein the polyoxyalkylene diimide diacid is derived from one or more polyoxyalkylene diiamines and one or more tricarboxylic acid compounds containing two vicinal carboxyl groups or an anhydride group and an additional carboxyl group, and is characterized by the following formula:

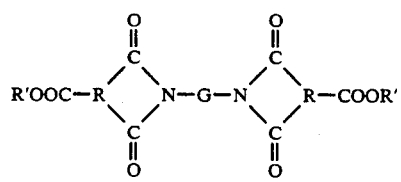

wherein each R is independently selected from a member of the group consisting of $C_2$ to $C_{20}$ aliphatic trivalent organic radicals, $C_2$ to $C_{20}$ cycloaliphatic trivalent organic radicals, and $C_6$ to $C_{20}$ aromatic trivalent organic radicals; each R' is independently selected from the group consisting of hydrogen, $C_1$ to $C_6$ aliphatic and cycloaliphatic monovalent organic radicals, and $C_6$ to $C_{12}$ aromatic monovalent organic radicals, and G is the radical remaining after removal of the hydroxy groups of a long chain ether glycol having an average molecular weight of from about 600 to 12000.

7. A suture according to claim 1 further comprising a member selected from the group consisting of stabilizers and at least one medico-surgically useful substance.

8. A suture according to claim 1 further comprising a human growth factor.

9. A suture according to claim 1 wherein the suture is a monofilament suture.

10. A suture according to claim 1 wherein the suture is a multifilament suture.

11. A suture according to claim 1 wherein the suture is a dyed suture.

12. A suture according to claim 1 wherein the polyetherimide ester composition comprises at least about 50 mole percent the reaction product of
   a) 1,4 butanediol;
   b) dimethyl terephthalate; and
   c) a polyoxyalkylene diimide diacid.

13. A suture according to claim 1 wherein the polyethermide ester composition comprises at least about 70 mole percent the reaction product of
   a) 1,4 butanediol;
   b) dimethyl terephthalate; and
   c) a polyoxyalkylene diimide diacid.

14. A suture manufactured from a resin comprising the reaction product of
   a) 1,4 butanediol;
   b) dimethyl terephthalate; and
   c) a polyoxyalkylene diimide diacid derived from trimellitic anhydride and a polyoxyalkylene diimide having the formula $NH_2$—G—$NH_2$, wherein G is the divalent radical remaining after removal of the hydroxy groups of a long chain ether glycol having a molecular weight of from about 900 to about 4000.

15. A suture according to claim 14 wherein the long chain ether glycol is selected from a member of the group consisting of polypropylene ether glycol and co(polyethylene ether-propylene ether) glycol having a predominantly polyethylene ether backbone.

* * * * *